US010531938B2

(12) United States Patent
Vollmann et al.

(10) Patent No.: US 10,531,938 B2
(45) Date of Patent: Jan. 14, 2020

(54) METHOD FOR THE PRODUCTION OF A DENTAL RESTORATION

(71) Applicant: DENTSPLY SIRONA Inc., York, PA (US)

(72) Inventors: Markus Vollmann, Gelnhausen (DE); Lothar Volkl, Goldbach (DE); Stefan Fecher, Johannesberg (DE); Carsten Wiesner, Rockenberg (DE)

(73) Assignee: DENTSPLY SIRONA INC., York, PA (US)

(*) Notice: Subject to any disclaimer, the term of this patent is extended or adjusted under 35 U.S.C. 154(b) by 66 days.

(21) Appl. No.: 15/786,631

(22) Filed: Oct. 18, 2017

(65) Prior Publication Data

US 2018/0104031 A1    Apr. 19, 2018

(51) Int. Cl.
| | |
|---|---|
| *A61C 13/00* | (2006.01) |
| *A61C 13/08* | (2006.01) |
| *A61K 6/02* | (2006.01) |
| *C03C 10/00* | (2006.01) |
| *C03C 4/00* | (2006.01) |
| *A61C 13/083* | (2006.01) |
| *C03C 3/097* | (2006.01) |

(Continued)

(52) U.S. Cl.
CPC ...... *A61C 13/0022* (2013.01); *A61C 13/0003* (2013.01); *A61C 13/081* (2013.01); *A61C 13/083* (2013.01); *A61K 6/0255* (2013.01); *C03C 3/097* (2013.01); *C03C 4/0021* (2013.01); *C03C 10/0027* (2013.01); *A61C 8/0012* (2013.01); *A61C 13/04* (2013.01); *A61K 6/0612* (2013.01); *C04B 41/51* (2013.01)

(58) Field of Classification Search
None
See application file for complete search history.

(56) References Cited

U.S. PATENT DOCUMENTS

2012/0309607 A1* 12/2012 Durschang ............. A61K 6/024
501/59
2014/0000314 A1    1/2014 Ritzberger et al.
(Continued)

FOREIGN PATENT DOCUMENTS

| CA | 2911284 A1 | 11/2014 |
|---|---|---|
| DE | 1458477 A1 | 1/1969 |

(Continued)

OTHER PUBLICATIONS

International Search Report of PCT/EP2017/076531 dated Jan. 16, 2018.

*Primary Examiner* — Mary Lynn F Theisen
(74) *Attorney, Agent, or Firm* — Dentsply Sirona Inc.

(57) ABSTRACT

The invention relates to a method for the production of a restoration from a blank consisting of, or containing, a lithium silicate glass ceramic, wherein at least two layers of ceramic material of different compositions are filled into a mold layer-by-layer and after filling of the layers they are then pressed and sintered, wherein after filling of a first layer this is structured on its surface in such a way that the first layer, viewed across its surface, differs in its height from region to region, and then a layer with a composition that differs from the first layer is filled as a second layer into the mold. After sintering the dental restoration is produced from the blank by mechanical working.

22 Claims, 4 Drawing Sheets

(51) Int. Cl.
*A61C 8/00* (2006.01)
*A61C 13/01* (2006.01)
*A61K 6/06* (2006.01)
*C04B 41/51* (2006.01)

(56) References Cited

U.S. PATENT DOCUMENTS

| | | |
|---|---|---|
| 2015/0140274 A1 | 5/2015 | Burke et al. |
| 2015/0173869 A1 | 6/2015 | Jung et al. |
| 2016/0081777 A1 | 3/2016 | Yamada et al. |
| 2017/0189146 A1* | 7/2017 | Volkl ................... A61C 5/77 |
| 2017/0273764 A1* | 9/2017 | Volkl ................ A61C 13/0022 |

FOREIGN PATENT DOCUMENTS

| | | |
|---|---|---|
| DE | 19750794 A1 | 6/1999 |
| DE | 10336913 B4 | 1/2014 |
| EP | 1149058 B1 | 2/2015 |
| JP | 2004035332 A | 2/2004 |
| WO | 2013053865 A2 | 4/2013 |

* cited by examiner

METHOD FOR THE PRODUCTION OF A DENTAL RESTORATION

THE CROSS-REFERENCE TO RELATED APPLICATIONS

This patent application claims the benefit of and priority to German Patent Application No. 102016119935.4, filed on Oct. 19, 2016, which is herein incorporated by reference for all purposes.

TECHNICAL FIELD

The invention relates to a method for the production of a dental restoration from a blank consisting of, or containing, lithium silicate glass ceramic, wherein at least one starting lithium silicate glass is melted, the glass melt is quenched and comminuted to a powder and the powder pressed to a body and the body sintered to produce the blank.

The invention also relates to the use of a blank for the production of a dental restoration.

BACKGROUND OF THE INVENTION

EP 1 149 058 B1 discloses a method for the production of a dental product of lithium disilicate, wherein a lithium silicate glass melt is poured into a steel mold and is cooled, so that temperature treatment is then used to transform the glass into a glass ceramic. The glass ceramic is then comminuted to a powder and compressed, and the blank so produced is pre-sintered. The blank is then heated and pressed into a mold to yield a dental restoration.

DE 103 36 913 B4 discloses the use of a lithium silicate blank which contains lithium metasilicate as a main crystal phase and is intended for the production of a dental restoration. To produce the blank, the glass melt is poured into a mold to obtain a block which is then subjected to heat treatment to provide a lithium metasilicate glass ceramic blank, so that a dental restoration can be derived from this, for example through milling or grinding.

DE 197 50 794 A1 discloses a lithium disilicate glass ceramic product. A dental product can thereby be derived from a blank, which has been produced by casting a melt into mold, through hot pressing or computer-controlled milling. The dental restoration derived through mechanical working then has to undergo further heat treatment to achieve the desired strength.

US 2014/000314 A1 refers to a lithium silicate glass ceramic and glass with $ZrO_2$ content. Lithium silicate glass is melted in order to then produce a glass frit. Granulate is pressed and sintered. Cylindrical glass blanks are produced which are then subjected to a heat treatment. From the blanks are then produced dental restorations by means of hot-pressing or a CAD/CAM method.

EP 1 149 058 B1 refers to a method for making pressable lithium disilicate glass ceramics. A glass ceramic powder is pressed, whereby blanks may be machined to a dental restoration of desired geometry.

WO 2013/053865 A2 refers to a lithium silicate glass ceramic and a lithium silicate glass comprising a trivalent metal oxide. A powder pellet is produced, in order to subsequently perform a controlled crystallization. From the pellet dental restorations are produced by means of a CAD/CAM method.

The aim of the present invention is to further develop a method using a blank of the above-described type in such a way that dental restorations of the desired dimensions are made available without difficulty, wherein with simple measures a desired coloration and/or translucency can be obtained where necessary. In particular, it is intended that after production of the dental restoration from a blank there is no need for further heat treatment steps.

SUMMARY OF THE INVENTION

To achieve this aim the invention in the main provides for at least two layers of powders, which have been derived from starting lithium silicate glasses of different compositions, to be filled into a mold layer-by-layer, wherein after introduction of a first layer the surface of this layer is structured such that the first layer viewed across its surface varies in its height from one region to another, and then as the second layer a layer with a composition that differs from that of the first layer is filled into the mold, or that after introduction of the first layer a further layer of a powder is filled into the mold that differs in its composition from the first layer, that the material of the first layer is mixed with the material of the further layer to form an intermediate layer, and that the second layer is then filled into the mold, and that then after introduction of the layers they are pressed and then sintered to yield a blank, and that the dental restoration is produced from the blank through mechanical working.

A blank derived from pressed powder, which is machine-worked, for example through grinding or milling, is used to derive a desired dental restoration. No poured blocks are used.

Since pressed powder is used for the blank, an individual coloration or translucency can be achieved without difficulty, in that powders of different color and/or translucency properties are mixed together to the desired degree and then pressed. It is thereby possible to introduce powders of different compositions layer-by-layer into a mold and to thereby derive a blank that has regions of different translucency properties and/or color properties. It is in particular provided for the blank to have a transition region between layers of different translucency and/or coloration that virtually joins the layers continuously.

The invention in particular provides for the structuring of the surface of the first layer after it has been formed such that the first layer when viewed along its surface has regions that differ in their height, i.e., do not have a uniform fill height, and then for the second layer that differs from the first layer in its composition to be filled into the mold.

As an alternative, it is possible after introduction of the first layer for the intermediate layer of a powder that is similarly produced from a starting lithium silicate glass to be filled into the mold, wherein the powder differs from that of the first layer, that the material of the first layer is mixed with the material of the intermediate layer and that the second layer is then filled into the mold. It is in particular provided here for the material of the intermediate layer to be mixed with that of the first layer starting from the free surface of the intermediate layer over a height that is twice or approximately twice the height of the intermediate layer. Further, it is in particular provided for the material of the intermediate layer to be the same as that of the second layer.

In accordance with the invention, with the first alternative a first layer of pourable material is filled into a mold. After filling of the powder, which has a grain size of between 1 μm and 150 μm, preferably between 10 μm and 30 μm, the surface is smoothed to yield a structure which has elevations and valleys that in particular extend parallel to one another and in particular however extend concentrically or parallel to one another. It is provided in particular for this purpose for the structure to be formed through an element that moves relative to the first layer, in particular rotates, which is structured in its surface region in particular with a wave-like, comb-like or saw-tooth-like section. There is virtually a "roughening" or "scratching" of the surface to form the structure, i.e., the alternating elevations and depressions.

It is in particular provided for the structure to be formed such that the volume of the elevations is equal to, or approximately equal to, the volume of the depressions/valleys.

The saw-tooth-shaped element should preferably have V-shaped teeth that are symmetrically formed with flanks which include an angle between 15° and 45°. The distance between neighboring teeth, i.e., from one peak to the next, should be between 1 mm and 4 mm, preferably between 1 mm and 3 mm.

The pourable second ceramic material is then filled into the mold, said material increasing in quantity from the depressions of the structure formed by the valleys, so that as a consequence thereof there is a virtually continuous increase in the proportion of the second layer across the height of the elevations. After smoothing of the surface the layers are pressed. There is then a pre-sintering or sintering to a full density at a temperature between 650° C. and 760° C. or between 750° C. and 950° C. for a time period, for example, between 5 and 120 minutes. Prior to this, or at the same time as pre-sintering or sintering to full density, at least one crystallization step can be carried out to form lithium metasilicate crystals or lithium disilicate crystals therefrom. Naturally, there is no departure from the invention if the crystallization step is carried out with the glass frit from which the powder is produced. The teaching according to the invention also includes the possibility of performing a further crystallization step after mechanical working.

The blank produced from the pressed body, i.e., after pre-sintering or sintering to full density, is then worked, for example through milling and/or grinding, to yield a desired dental restoration.

Sintering to full density is carried out, for example, over a period of time between 5 and 120 minutes at a temperature in the range 750° C. to 950° C.

The penetration of the layers brings the advantage that at least different optical characteristics can be achieved over the height of the blank. Thus, once the first layer has been colored to a desired degree, after sintering to full density a tooth-colored boundary region is obtained, in which via the transition region caused by the penetrating first and second layer materials, the intensity of the tooth color continuously reduces and at the same time the translucency increases in the desired manner. The dental restoration is then derived from the blank in particular through milling, taking the course of the layers into consideration, wherein the dental restoration is "laid" in the blank so that the incisal part of the tooth extends in the region of the second layer.

Independently thereof, on the basis of the teaching according to the invention, there is a continuous transition between the layers so that the color/translucency continuously decreases/increases. There is no abrupt transition but as already mentioned a continuous, i.e., virtually constant transition across the height of the dental restoration to be produced.

In a preferred manner the invention provides for the possibility of mixing of the layer materials, whereby an element is rotated about an axis extending along the longitudinal axis of the mold, to achieve the structure, also referred to as being wave-like or saw-tooth-like, through displacement of material of the surface of the first layer.

There is also the possibility of forming the structure through a pressure element also referred to as stamp that acts in the direction of the surface on the first layer, that in particular has elevations extending in its surface with depressions extending between them, so that the negative shape of the element is impressed into the surface of the first layer. Then—as already described—the ceramic material of the second layer is filled in, then smoothed to exclusively press the layers together and to then pre-sinter the pressed object.

The invention is also characterized in that the first and second layers in their connecting region are penetrated across a height H which is between 1/15 and one quarter, in particular between 1/10 and 1/5 of the total height of the first and second layers.

The first layer in an unstructured state should have a height that is approximately ½ to ⅔ of the sum of the first and second layers.

In particular the invention is characterized in that a starting glass is used that has a composition that contains, or consists of, the following in percentage by weight:

| | |
|---|---|
| $SiO_2$ | 57.5-60.5 |
| $Li_2O$ | 13.5-20.5 |
| $ZrO_2$ | 8.5-11.5 |
| $P_2O_5$ | 3.0-7.5 |
| $Al_2O_3$ | 0.5-6.0 |
| $K_2O$ | 0.5-3.5 |
| $CeO_2$ | 0.5-2.5 |
| $B_2O_3$ | 0-3.0 |
| $Na_2O$ | 0-3.0 |

At least one additive 0-4.

The composition preferably contains or consists of the following in percentage by weight:

| | |
|---|---|
| $SiO_2$ | 57.5-60.5 |
| $Li_2O$ | 14.0-16.0 |
| $ZrO_2$ | 9.0-10.5 |
| $P_2O_5$ | 5.0-6.0 |
| $Al_2O_3$ | 2.5-3.0 |
| $K_2O$ | 1.0-1.5 |
| $CeO_2$ | 0.5-1.0 |
| $B_2O_3$ | 2.5-3.0 |
| $Na_2O$ | 0.1-2.0 |
| $V_2O_5$ | 0.1-0.7 |
| $Er_2O_3$ | 0-1.0 |
| $Y_2O_3$ | 0.3-0.5 |
| $MnO_2$ | 0-0.2. |

The sum of the components for the starting glass amounts to 100% by weight.

To achieve a mean grain size between 1 µm and 150 µm, in particular between 10 µm and 30 µm of the powder to be pressed, the invention provides for a powder that is derived from frit and to be sieved with a sieve with a mesh between 50 µm and 250 µm. Where required, further milling can be carried out, for example through a jet mill or an attrition mill (Attritor).

To influence fluorescence/color, the corresponding metal oxides (for example rare earth oxides) are added to the starting material. So, for example, $Tb_2O_3$ and/or $Er_2O_3$ can be used to influence the fluorescence and, for example, $MnO$, $Fe_2O_3$, $Y_2O_3$, $V_2O_3$, $CeO_2$ or other rare earth oxides can be used to influence the coloration.

The invention is also characterized through the use of a blank to produce a dental restoration through mechanical/machine working of the blank, wherein the blank consists of, or contains, a sintered body of pressed silicate glass ceramic powder.

A use that is in particular intended is one in which the body and/or the blank is subject to at least one crystallization step.

A preferred use is one in which the lithium silicate glass percentage of the blank is in the range 20 to 80% by volume.

The lithium metasilicate phase can be between 10 and 70% by volume of the crystal phase. The disilicate phase can lie between 10% and 95% by volume of the crystal phases. Lithium phosphate may also be contained as a crystal phase.

BRIEF DESCRIPTION OF THE DRAWINGS

Further details, advantages and characteristics of the invention result not only from the claims and their features, both by themselves and/or in combination, but also from the following description of the preferred example embodiments and from the drawings.

DETAILED DESCRIPTION OF THE INVENTION

The teaching according to the invention is described with reference to FIG. 1, in which the same elements are given the same reference numbers, on the basis of which the dental restorations are produced from lithium silicate glass ceramic, and have a monolithic structure such that after full sintering a monolithic tooth prosthesis is available that can be used directly. For this purpose it is provided according to the invention for a blank to be produced that consists of a number of layers of powders that are derived from a starting lithium silicate glass, with compositions that differ from one another, through which in particular desired optical characteristics can be achieved which correspond to the dental restoration to be produced, leading to a direct use of the tooth prosthesis without it being necessary, for example, for an incisal layer to be manually applied and burned after full sintering.

A first ceramic material 14 is initially produced that is made from a lithium silicate glass ceramic. For this a starting glass powder with a composition in percentage by weight given below is melted:

| | |
|---|---|
| $SiO_2$ | 57.5-60.5 |
| $Li_2O$ | 13.5-20.5 |
| $ZrO_2$ | 8.5-11.5 |
| $P_2O_5$ | 3.0-7.5 |
| $Al_2O_3$ | 0.5-6.0 |
| $K_2O$ | 0.5-3.5 |
| $CeO_2$ | 0.5-2.5 |
| $B_2O_3$ | 0-0 3 |
| $Na_2O$ | 0-3 |

At least one additive 0-4.

The minimum of one additive is at least one additive from the group color pigments and/or fluorescence agents. It is in particular provided for the additive to be at least one oxide from the group of rare earth metals or for it to contain one such oxide.

The corresponding mixture of starting materials is then melted in a suitable crucible of fire-resistant material or noble metal alloy at a temperature between 1350° C. and 1600° C. for a time period between 1 hour and 10 hours, in particular for a time period between 4 hours and 7 hours at a temperature of 1540° C. Homogenization is carried out either at the same time or thereafter, for example through stirring. The liquid glass so derived is then quenched in a suitable medium such as water or high-temperature wool. The quenched glass frit so produced is then dried. It is then milled, for example in a ball mill. It is then sieved, for which a sieve with a mesh size between 50 µm and 250 µm can be used. If necessary it can be milled further, for example using a jet mill or an attrition mill (Attritor).

From the glass powder or glass particle powder so produced, those particles with a grain size between 1 µm and 150 µm are removed by sieving.

To allow the blank to be worked without difficulty, without the molded part produced from the blank being unstable upon full sintering, a crystallization step is performed either for the frit obtained after melting or for the powder after pre-milling or final milling. Thereby in a first heat treatment step the frit/the powder is subjected to a temperature $T_1$ between 500° C. and 750° C. for a time $t_1$ between 5 minutes and 120 minutes. The first heat treatment step can also be carried out in two stages, i.e., initially at 640° C. and preferably 660° C. for 60 minutes and then at 750° C. for 40 minutes.

In a preferred manner this is followed by a further heat treatment in the form of tempering, whereby the chosen temperature $T_3$ should lie between 750° C. and 900° C. The temperature step is carried out over a time $t_3$ in particular for between 5 and 30 minutes.

There is naturally no departure from the invention if a binding agent is added to the starting powder. It is, however, preferred if no binding agent is used.

The production of a blank, from which a dental restoration can be produced, is now described with reference to FIGS. 1 and 2. Thus a first powder 14 is initially filled into a mold 10 of a press 12 in accordance with FIG. 1*a*).

A second layer 24 of a second powder is then produced as described before, but with a composition that differs from that of the first powder, and is filled into the mold 10 (FIG. 1*c*)), wherein the total height of the layers 14 and 24 is twice the height of the layer 14 in an unstructured state, without any resultant limitation of the teaching according to the invention.

If the first layer 14 preferably has a height that corresponds to half the total height H of the first and second layers 14, 24, then the height of the first layer 14 can also be ½ H to ⅔ H and thus that of the second layer 24 can be ⅓ H to ½ H.

The smoothed surface is then structured in accordance with step b). For this purpose an element 16 that is disc-shaped, plate-shaped or web-shaped is used, which in the example embodiment on the layer side has a serrated geometry, so that a corresponding negative structure is formed in the surface 18 of the layer 14 through the displacement of material. This structure takes the form of concentrically extending elevations and surrounding valleys. The distance between an elevation (peak) and valley (depression), i.e., the clearance between projection 20 and valley base 22 according to FIG. 2 is approximately ⅕ of the height of all layers.

The invention in particular provides for the structure to be formed in such a way that the volume of the elevations is equal to, or approximately equal to, the volume of the depressions/valleys.

Figure 1:
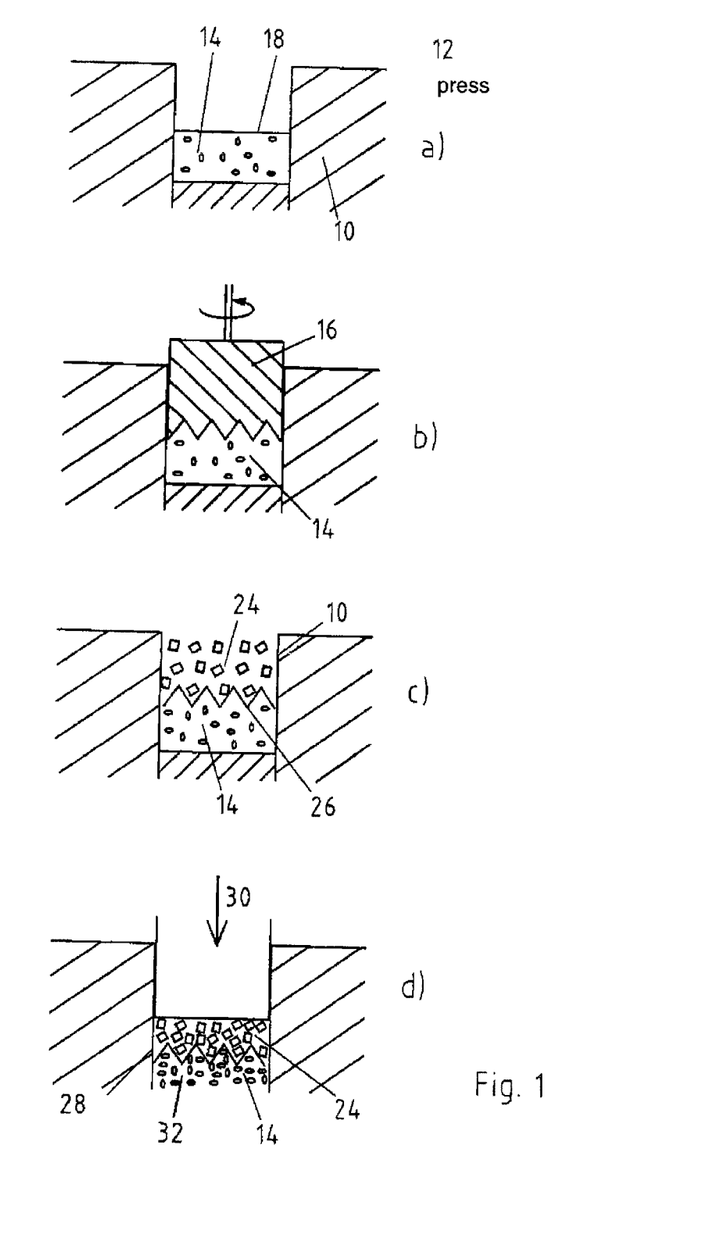
FIG. 1 A schematic of an assembly and the method steps that can be carried out using it, FIG. 2 An enlarged view of FIG. 1*b*), FIG. 3 A schematic of a bridge to be produced from a blank, and FIG. 4 A schematic of an alternative method
Figure 2:
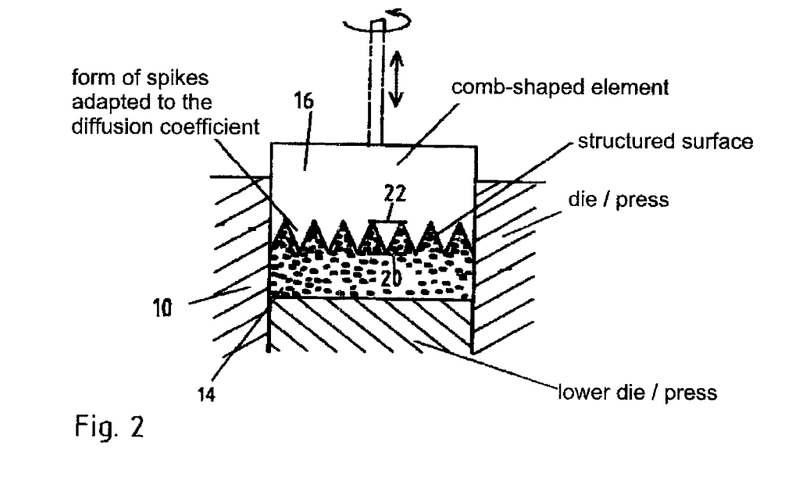

Because the material of the second layer 24 penetrates into the base of the valleys 26 in the surface 18 of the layer 14, there is a continuous transition between the properties of the layer 14 and the layer 24, after the layers 24, 14 have been pressed according to FIG. 1d). The transition layer or intermediate layer is indicated by the reference number 28 in FIG. 1d).

The layer 24 is made of a material that differs from that of the layer 14. The difference is due in particular to the color additives.

The percentage of color oxides in the layer 24 is reduced compared to layer 14. As a result of this measure there is a continuous color transition between the layers 14 and 24.

The layers 14, 24 are pressed by means of a stamp, with pressing carried out at a pressure between 50 MPa and 400 MPa.

The blank 33 produced is forced out of the mold 10 after pressing and is then pre-sintered or fully sintered in the usual manner.

Figure 3:
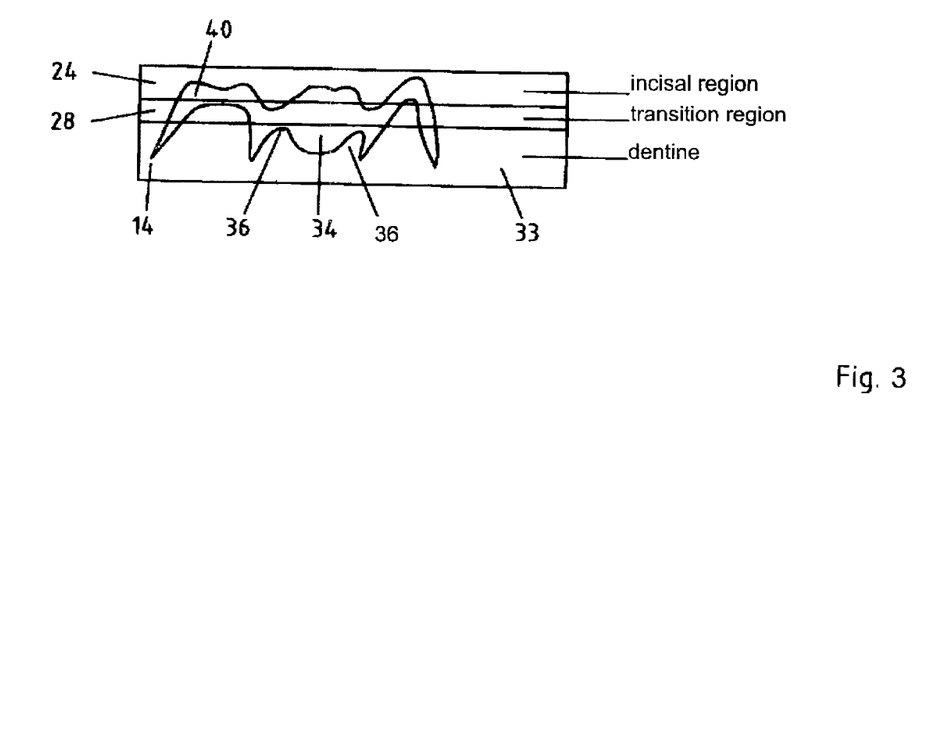

If a dental prosthesis is milled from the blank 33—in the example embodiment a bridge 34—then the milling program is designed such that the lower region of the bridge 34 extends in the layer 14 and the cutting region 40 of the bridge extends in the layer 24.

In the transition region, i.e., in the central layer 28, in which there is a virtually constant/continuous transition between the layers 14 and 24, there is the transition between dentine and incisal region. The dentine extends in the region 14.

An alternative method is described with reference to FIG. 4 which follows the teaching according to the invention, to enable production of a blank or dental restoration that offers a substantially continuous transition between a first layer and a second layer or in the case of a restoration between the dentine and incisal regions in terms of translucency and strength.

Figure 4:
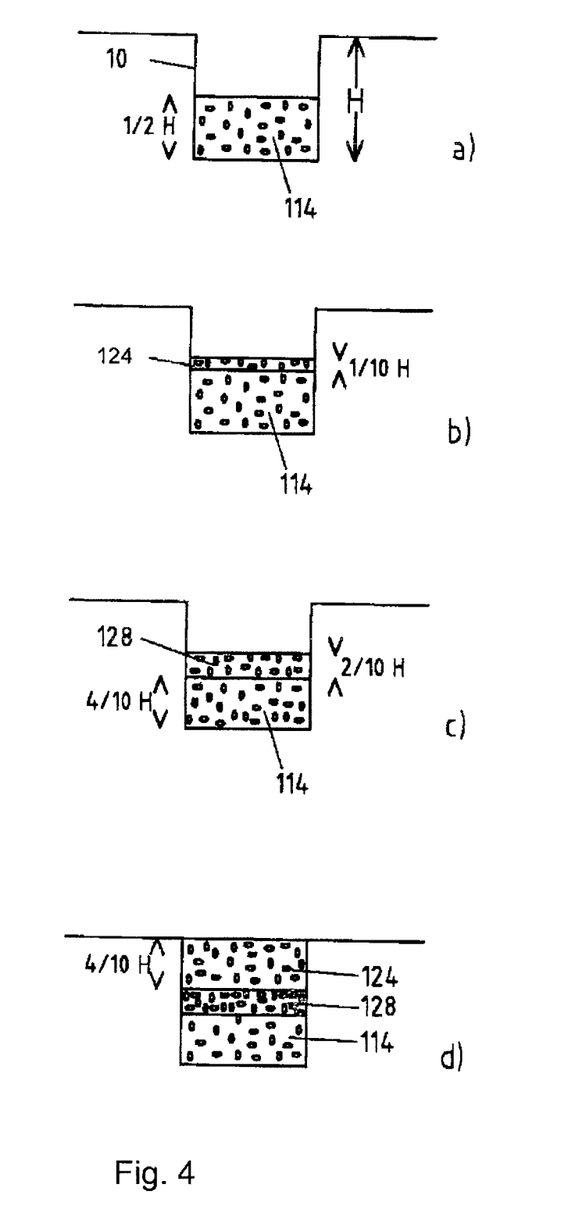

Thus in accordance with FIG. 4a a first powder is filled into a mold 10, which can correspond to that of layer 14 according to FIG. 1. The corresponding layer in FIG. 4a is indicated by the number 114. The height of this layer 114 can correspond to half the height of the total layers that are filled into the mold 10. A layer 127 is then laid on to the layer 114 with a thickness that in the example embodiment is ¹⁄₁₀ of the total height of the layers. The material of the layer 127 can correspond to that of the second layer 24 according to FIG. 1. There is then a mixing of the layer 127 with a surface region of the layer 114 over a depth that corresponds to the thickness of the layer 127. As a result, an intermediate layer 128 is formed that has a thickness that is ²⁄₁₀ of the entire height of the layers. A further layer 124, which corresponds to the second layer 24 according to FIG. 1, is then applied to the intermediate layer 128. The height of the layer 124 in the example embodiment is thus ⁴⁄₁₀ of the total height H. Then, in accordance with the example embodiment of FIG. 1, all the layers 124, 128, 114 together are pressed so that the method steps of pre-sintering, working and full sintering are then carried out, as has been explained. Naturally, working can also be carried out after sintering to full density.

The present invention may include one or more of the following features and/or combinations:

1. A method for the production of a restoration (34) from a blank (33) consisting of, or containing, a lithium silicate glass ceramic, wherein at least one starting lithium silicate glass is melted, the glass melt is cooled rapidly and is comminuted to a powder,
characterized in that
at least two layers (14, 24) of powders, which are produced from starting lithium silicate glasses of different compositions, are filled into a mold layer-by-layer, wherein after filling of a first layer (14) its surface is structured in such a way that the first layer (14) viewed across its surface (18) varies in its height from one region to another and then as the second layer (24) a layer with a composition that differs from that of the first layer is filled into the mold, or that after introduction of the first layer (114) a further layer (127) of a powder is filled onto it in the mold (10) that differs from the first layer in terms of composition, that the material of the first layer is mixed with the material of the further layer to form an intermediate layer (128) and that the second layer (124) is then filled into the mold (10),
and that after introduction of the layers they are pressed and then sintered to form a blank, and that the dental restoration is produced from the blank by mechanical working.

2. The method according to claim 1,
characterized in that
the surface (18) of the first layer (14) is structured such that elevations separated by depressions are formed.

3. The method according to at least claim 1 or 2,
characterized in that
a ring structure is formed in the surface (18) in top view which has the elevations separated by the depressions.

4. The method according to at least claim 1,
characterized in that
the structure is created by an element (16) that moves, in particular rotates, relative to the first layer (14), that in particular structures the surface region of the first layer (14) through a wave-like, comb-like or saw-tooth-like region.

5. The method according to at least claim 1,
characterized in that
the structure is created by a pressure element acting in the direction of the surface (18) of the first layer (14).

6. The method according to at least claim 5,
characterized in that
a pressure element is used which results in concentrically extending or parallel-extending elevations with depressions extending between them being pressed into the surface (18) of the first layer (14).

7. The method according to at least claim 1,
characterized in that
the structure is formed such that the volume of the elevations is equal to, or approximately equal to, the volume of the depressions.

8. The method according to at least claim 1,
characterized in that
the material of the further layer (127) is mixed with that of the first layer (114) commencing from the free surface of the further layer over a height that corresponds to twice, or approximately twice the height of the further layer.

9. The method according to claim 1,
characterized in that
the body is fully sintered.

10. The method according to at least claim 1,
characterized in that
the starting glass used has a composition which contains, or consists of, in percentage by weight:

|  |  |
| --- | --- |
| $SiO_2$ | 57.5-60.5 |
| $Li_2O$ | 13.5-20.5 |
| $ZrO_2$ | 8.5-11.5 |
| $P_2O_5$ | 3.0-7.5 |
| $Al_2O_3$ | 0.5-6.0 |
| $K_2O$ | 0.5-3.5 |
| $CeO_2$ | 0.5-2.5 |
| $B_2O_3$ | 0-3.0 |
| $Na_2O$ | 0-3.0 |

At least one additive 0-4.

The invention claimed is:

1. A method for the production of a restoration from a blank that includes a lithium silicate glass ceramic, the method comprising the steps of:
    filling into a mold layer-by-layer at least two layers of powders, each powder being produced from starting lithium silicate glasses of different compositions, including the steps of:
       filling the mold with a first layer of a first powder material, the first layer having a surface that is structured in such a way that when the first layer is viewed across, the surface varies in height from one region to another region;
       after introduction of the first layer, filling the mold with a second layer of a second powder material that differs from the first powder material of the first layer in terms of composition, wherein a portion of the second powered material of the second layer is displaced within the surface of the first layer that varies in height from one region to another region to form an intermediate layer of the first powder material from a portion of the first layer that is mixed with the second powder material from a portion of the second layer;
    after introduction of the at least two layers, the at least two layers are pressed to form a body and then sintered to form a blank; and
    mechanically working the blank to form the restoration.

2. The method according to claim 1, wherein the surface of the first layer is structured such that elevations separated by depressions are formed.

3. The method according to claim 1, wherein a ring structure is formed in the surface in top view which has the elevations separated by the depressions.

4. The method according to claim 1, wherein the structure is created by an element that moves relative to the first layer through a wave-like, comb-like or saw-tooth-like region.

5. The method according to claim 1, wherein the structure is created by a pressure element acting in the direction of the surface of the first layer.

6. The method according to claim 5, wherein a pressure element is used which results in concentrically extending or parallel-extending elevations with depressions extending between them being pressed into the surface of the first layer.

7. The method according to claim 1, wherein the structure is formed such that the volume of the elevations is equal to, or approximately equal to, the volume of the depressions.

8. The method according to claim 1, wherein the material of the second layer is mixed with that of the first layer commencing from the free surface of the second layer over a height that corresponds to twice, or approximately twice the height of the second layer.

9. The method according to claim 1, wherein the body is fully sintered.

10. The method according to claim 1, wherein the starting glass used has a composition which includes, in percentage by weight:

| | |
|---|---|
| $SiO_2$ | 57.5-60.5 |
| $Li_2O$ | 13.5-20.5 |
| $ZrO_2$ | 8.5-11.5 |
| $P_2O_5$ | 3.0-7.5 |
| $Al_2O_3$ | 0.5-6.0 |
| $K_2O$ | 0.5-3.5 |
| $CeO_2$ | 0.5-2.5 |

11. The method according to at least claim 1, characterized in that the composition contains, or consists of, in percentage by weight:

| | |
|---|---|
| $SiO_2$ | 57.5-60.5 |
| $Li_2O$ | 14.0-16.0 |
| $ZrO_2$ | 9.0-10.5 |
| $P_2O_5$ | 5.0-6.0 |
| $Al_2O_3$ | 2.5-3.0 |
| $K_2O$ | 1.0-1.5 |
| $CeO_2$ | 0.5-1.0 |
| $B_2O_3$ | 2.5-3.0 |
| $Na_2O$ | 0.1-2.0 |
| $V_2O_5$ | 0.1-0.7 |
| $Er_2O_3$ | 0-1.0 |
| $Y_2O_3$ | 0.3-0.5 |
| $MnO_2$ | 0-0.2. |

12. The method according to at least claim 1, characterized in that the frit formed through quenching and/or the powder prior to pressing and/or the pressed powder are subject to at least one crystallization step.

13. The method according to at least claim 1, characterized in that the powder is pressed without binding agents.

14. The method according to at least claim 1, characterized in that the powder to be pressed is sieved through a sieve with a mesh size between 50 µm and 250 µm to obtain a mean grain size between 1 µm and 150 µm, in particular between 10 µm and 30 µm.

15. The method according to at least one of the above claims characterized in that to influence the color of the dental restoration at least one oxide of the rare earth metals is added to the starting material.

16. The method according to at least one of the above claims characterized in that to influence opalescence crystals of the crystal phases have a maximum length between 10 nm and 800 nm.

17. An use of a blank (33) to manufacture a dental restoration (34) through mechanical working of the blank, wherein the blank consists of, or contains, a sintered body of pressed lithium silicate glass ceramic powder.

18. The use according to claim 17, in which the body and/or the blank (33) is subject to at least one crystallization step.

19. The use according to claim 17 or 18, wherein the lithium silicate glass is present in the blank (33) in the range 20 to 80% by volume.

20. The use according to at least one of claims 17 to 19, wherein the blank (33) contains crystal phases, wherein the lithium metasilicate phase of the crystal phases of the blank is in the range 10 to 70 percent by volume and/or the lithium disilicate phase of the crystal phases of the blank is in the range 10 to 95 percent by volume.

21. The use according to at least claim 17, wherein the mechanical working includes at least grinding and/or milling.

22. The use according to at least claim 17, wherein the blank (33) is a pressed body that is free of binding agents.

-continued

|  |  |
|---|---|
| B$_2$O$_3$ | 0-3.0 |
| Na$_2$O | 0-3.0 |

At least one additive 0-4.

11. The method according to claim 1, wherein the starting glass used has a composition that includes, in percentage by weight:

|  |  |
|---|---|
| SiO$_2$ | 57.5-60.5 |
| Li$_2$O | 14.0-16.0 |
| ZrO$_2$ | 9.0-10.5 |
| P$_2$O$_5$ | 5.0-6.0 |
| Al$_2$O$_3$ | 2.5-3.0 |
| K$_2$O | 1.0-1.5 |
| CeO$_2$ | 0.5-1.0 |
| B$_2$O$_3$ | 2.5-3.0 |
| Na$_2$O | 0.1-2.0 |
| V$_2$O$_5$ | 0.1-0.7 |
| Er$_2$O$_3$ | 0-1.0 |
| Y$_2$O$_3$ | 0.3-0.5 |
| MnO$_2$ | 0-0.2. |

12. The method according to claim 1, formation of a frit from the powder through quenching and/or the powder prior to pressing and/or the pressed powder are subject to at least one crystallization step.

13. The method according to claim 1, wherein the powder is pressed without binding agents.

14. The method according to claim 1, wherein the powder to be pressed is sieved through a sieve with a mesh size between 50 μm and 250 μm to obtain a mean grain size between 1 μm and 150 μm.

15. The method according to claim 1, wherein to influence the color of the dental restoration at least one oxide of the rare earth metals is added to the starting glass material.

16. The method according to claim 1, wherein to influence opalescence crystals of the crystal phases have a maximum length between 10 nm and 800 nm.

17. An use of a blank to manufacture a dental restoration through mechanical working of the blank according to claim 1, wherein the blank comprises a sintered body of pressed lithium silicate glass ceramic powder.

18. The use according to claim 17, in which the body and/or the blank is subject to at least one crystallization step.

19. The use according to claim 17, wherein the lithium silicate glass is present in the blank in the range 20 to 80% by volume.

20. The use according to claim 17, wherein the blank includes crystal phases, wherein the lithium metasilicate phase of the crystal phases of the blank is in the range 10 to 70 percent by volume and/or the lithium disilicate phase of the crystal phases of the blank is in the range 10 to 95 percent by volume.

21. The use according to claim 17, wherein the mechanical working includes at least grinding and/or milling.

22. The use according to claim 17, wherein the blank is a pressed body that is free of binding agents.

* * * * *